United States Patent [19]

Takano et al.

[11] Patent Number: 5,219,743
[45] Date of Patent: Jun. 15, 1993

[54] METHOD FOR OPTICAL RESOLUTION OF COREY LACTONE DIOLS

[75] Inventors: Seiichi Takano; Tsutomu Sugahara, both of Sendai, Japan

[73] Assignee: Nissan Chemical Industries, Ltd., Tokyo, Japan

[21] Appl. No.: 836,377

[22] Filed: Feb. 18, 1992

[30] Foreign Application Priority Data

Feb. 27, 1991 [JP] Japan ................................. 3-55839

[51] Int. Cl.$^5$ ..................... C12P 17/04; C12P 41/00
[52] U.S. Cl. .................... 435/126; 435/280; 549/297; 549/299; 549/301; 549/302; 549/311; 549/312
[58] Field of Search ............... 435/280, 126; 549/297, 549/299, 301, 302, 311, 312

[56] References Cited

U.S. PATENT DOCUMENTS

| | | | |
|---|---|---|---|
| 3,778,450 | 12/1973 | Axen | 549/311 |
| 3,818,045 | 6/1974 | Kelly | 549/301 |
| 4,126,622 | 11/1978 | Tomoskozi et al. | 549/311 |
| 4,304,907 | 12/1981 | Nelson | 549/312 |
| 4,659,671 | 4/1987 | Klibanov | 435/280 |
| 4,745,066 | 5/1988 | Hamaguchi et al. | 435/280 |

FOREIGN PATENT DOCUMENTS

| | | |
|---|---|---|
| 0623319 | 5/1981 | Czechoslovakia ............... 549/311 |
| 261797 | 6/1989 | Czechoslovakia . |
| 0357009 | 3/1990 | European Pat. Off. . |
| 50-111074 | 9/1975 | Japan . |
| 52-105163 | 9/1977 | Japan . |
| 63-152339 | 6/1988 | Japan . |

OTHER PUBLICATIONS

Biotech Abs (92200402) Sugahara et all CPBTAL; Chem Pharm. Bull. pp. 2755-2760 (1991) 39,10.
Biotech Abs 91-13647 Hoechst DE4005150 Aug. 1991.
Biotech Abs 92-03423 Eastman Kodak EP-463680 Jan. 1992.
Biotech Abs 91-07384 Batiment EP-419988 Apr. 3, 1991.
Biotech Abs 91-07017 Naemura et al Chem Lett (1991)4, 657-60.
Biotech Abs 89-11532 Showa-Shell-JO1137996 May, 1989.
Biotech Abs 91-12380 Chisso EP-439779 Aug. 1991.
Biotech Abs 92-01975, J. Weidner, et al., "Synthesis of Enantiomerically Pure Prosaglandin Intermediates by Enzymatic Transesterification of (1S*,5R*,6R*,7R*)-($\pm$)-7-Hydroxy-6-hydroxymethyl-2-oxabicyclo[3.3.0]octan-3-one"; Liebigs Ann. Chem. 1991, pp. 1301-1303.
Chemical Abstracts, vol. 113, No. 5, Jun. 30, 1990, Columbus, Ohio, US; abstract No. 40320, Ivan Veseley et al.: "Resolution of a racemic Corey lactone via enantioselective esterification", p. 580.
Justus Liebigs Annalen der Chemie, vol. 1990, No. 10, Oct. 1990, K. Weinheim de Petzoldt et al.: "Mikrobiologische und enzymatische Reaktionsstufen in der Synthese von Prostacyclin-Analoga", pp. 1087-1091.
Chemical Abstracts, vol. 116, No. 19, May 11, 1992, Columbus, Ohio, US; abstract No. 193970, I. Veseley et (List continued on next page.)

[57] ABSTRACT

The primary hydroxy group of Corey lactone diols is optically selectively acylated to obtain the desired optically active ester and/or diol. The mixture of Corey lactone diols of formulae (Ia) and (Ib):

is reacted with an acylating agent optically selectively in the presence of an enzyme and/or a microorganism thereby to acylate, isolate and purify the primary alcohol.

8 Claims, No Drawings

OTHER PUBLICATIONS al.: "Resolution of a racemic Corey lactone via enantioselective esterification", p. 691.

*Collection of Czechoslovak Chemical Communications*, vol. 57, No. 2, 1992, Prague CS, pp. 357-361.

*Chemical and Pharmaceutical Bulletin*, vol. 39, No. 10, 1991, Tsutomu Sugahara et al.: "Efficient enzymatic preparation of (+)-and (−)-Corey lactone derivatives", Tokyo JP, pp. 2758-2760.

I. Tomoskozi et al., Regiospecific Prins Reaction, A New Way to Prostanoids, Central Research Institute for Chemistry, pp. 4639-4641.

E. J. Corey et al., Total Synthesis of Prostaglandins $F_{2a}$ and $E_2$ as the Naturally Occurring Forms, Journal of the American Chemical Society, Jan. 28, 1970, pp. 397-398.

E. J. Corey et al., Stereospecific Total Synthesis of Prostaglandins $E_3$ and $F_{3A}$, Journal of the American Chemical Society, Mar. 24, 1971, pp. 1490-1491.

Jasjit S. Bindra et al., New Extensions of the Bicyclo[2.2.1]Heptane Route to Prostaglandins, Journal of the American Chemical Society, Oct. 31, 1973, pp. 7522-7523.

*Primary Examiner*—Herbert J. Lilling
*Attorney, Agent, or Firm*—Oliff & Berridge

METHOD FOR OPTICAL RESOLUTION OF COREY LACTONE DIOLS

BACKGROUND OF THE INVENTION

1. Field of the Invention

The present invention relates to a method for optical resolution of Corey lactone diols which are intermediates of prostaglandins useful as drugs.

2. Description of Prior Art

Prostaglandins are physiologically active substances and play a fundamental role in maintaining homeostasis of the living body so that prostaglandins are expected to be utilized as drugs in various fields. Among them, prostaglandins have already been provided for practical use in the fields of oxytocia (rapid parturition), improvement in peripheral blood stream, anti-ulcer, prevention of platelet agglutination, etc.

The most effective method for chemical synthesis of prostaglandins comprises using as a key intermediate Corey lactones (formula [A]) reported by Corey et al.:

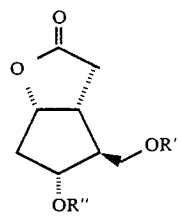

wherein R' and R" represent hydrogen atom or a hydroxy-protecting group (Reference publication: JACS, 92, 397 (1970), JACS, 93, 1490 (1971)).

Since many prostaglandins are synthesized still now via Corey lactones, Corey lactiones are compounds indispensable for synthesis of prostaglandins.

For synthesis of optically active Corey lactones, many methods are known. Among others, the following process is considered to be excellent.

1) Corey process ... synthetic process comprising as key steps Diels-Alder reaction of cyclopentadiene derivatives and optical resolution of hydroxycarboxylic acid (Reference Publications: JACS, 92, 397 (1970), JACS, 93, 1490 (1971)).

2) Chinoin process ... synthetic process comprising as a key step Prins reaction of optically active dicyclic lactones obtained by optical resolution (Reference Publications: Japanese Patent Application Laid-Open No. Sho 52-105163, Tetrahedron Letters (TL), 4639 (1976)).

3) Pfizer process ... synthetic process comprising as key steps Prins reaction of norbornadiene and optical resolution of carboxylic acids (Reference Publications: Japanese Patent Application Laid-Open No. Sho 50-111074, JACS, 95, 7522 (1973)).

4) Asymmetric Diels-Alder process ... synthetic process comprising as a key step asymmetric Diels-Alder reaction using an optically active pantholactone as an asymmetric source (Reference Publication: Japanese Patent Application Laid-open No. Sho 63-152339)).

The three processes 1) through 3) described above all require optical resolution and thus encounter problems that expensive agents for optical resolution should be used, operation for optical resolution such as salt formation, filtration, salt decomposition, recovery of agents used for optical resolution, etc. are complicated. The asymmetric Diels-Alder process 4) is excellent since Corey lactones can be produced in a high yield with high selectivity without optical resolution. After asymmetric reaction, however, the reaction steps for leading to Corey lactones are large in number. Therefore, the process was yet unsuitable as a process in an industrial scale.

For the foregoing reasons, a simpler method for optical resolution of Corey lactone esters has been desired.

SUMMARY OF THE INVENTION

The object of the present invention is to provide a method for optical resolution of optically active Corey lactone diols which are useful as intermediates for useful drugs, in one step.

DETAILED DESCRIPTION OF THE PREFERRED EMBODIMENTS

In view of the fact that Corey lactone diols of formulae (Ia) and (Ib):

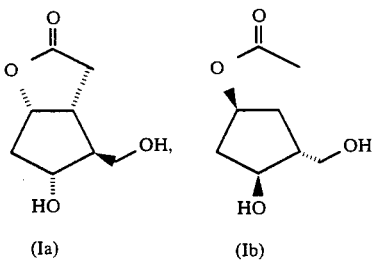

are useful compounds widely used for synthesis of drugs, agricultural chemicals, etc., the present inventors have made extensive investigations on an industrial method for optical resolution. As a result, the method of the present invention which is quite dissimilar to conventional methods and provides extremely easy operations has been attained.

Namely, the present invention relates to a method for optical resolution of optically active Corey lactone diols which comprises reacting a mixture of Corey lactone diols of the formulae (Ia) and (Ib) described above optically selectively with an acylating agent in the presence of enzyme and/or a microorganism capable of asymmetrically hydrolyzing a Corey lactone ester to acylate the primary hydroxy group of the diols, and isolating the remaining diols and the formed ester from each other and purifying them.

The present invention is expressed by the following reaction scheme:

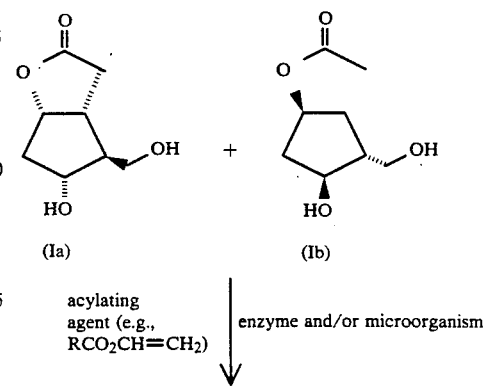

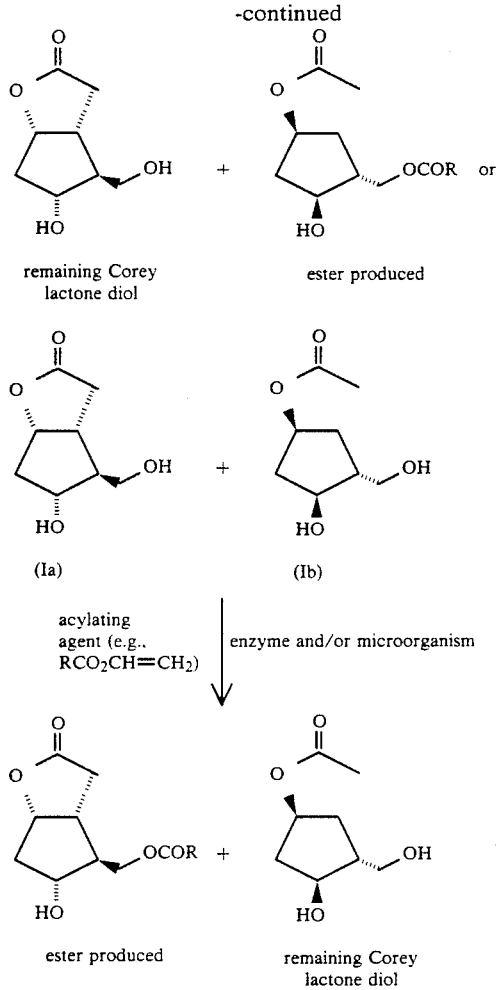

The enzyme which can be used in the present invention is an enzyme capable of asymmetically hydrolyzing an ester and obtained from a microorganism belonging to the genus Rhizopus, the genus Mucor, the genus Aspergillus, the genus Candida, the genus Pseudomonas, the genus Alcaligenes, the genus Acromobacter or the genus Bacillus or from animal organs. Examples include enzymes shown in Table 1.

The microorganism which can be used in the present invention is a microorganism belonging to the genus Rhizopus, the genus Mucor, the genus Aspergillus, the genus Candida, the genus Pseudomonas, the genus Alcaligenes, the genus Acromobacter or the genus Bacillus. Examples include microorganisms shown in Table 1 at the column entitled "Source".

TABLE 1

| Enzyme | Source | Company which sells or manufactures |
|---|---|---|
| Lipase AK | Pseudomonas sp. | Amano Pharmaceutical Co. |
| Lipase PS | " | " |
| Lipase "Amano" M10 | Mucor sp. | " |
| Lipase MAP 10 | " | " |
| Lipase AP6 | Aspergillus niger | " |
| Lipoprotein lipase "Amano" 40 (LPL) | Pseudomonas sp. | " |
| Lipase MY | Candida cyrindraceuous | The Meito Sangyo Co. Ltd. |
| Lipase CP | Candida paralipolytica | " |

TABLE 1-continued

| Enzyme | Source | Company which sells or manufactures |
|---|---|---|
| Lipase AL | Acromobacter sp. | " |
| Lipase PL266 | Alcaligenes sp. | " |
| Lipase PL679 | " | " |
| Olipase 4S | Rhizopus Japanicus | Osaka Bacterial Research Institute |
| Lipase "Saiken" 100 | Rhizopus Japanicus | Osaka Bacterial Research Institute |
| Lipase | Rhizopus niveus | Nagase Co. & Ltd. |
| Lipase | Rhizopus delemar | Seikagaku Kogyo Co., Ltd. |
| Protease (AF01) | Pig pancrease | Tokyo Kasei |
| Pancreatin | " | " |
| Lipase T | Rhizopus sp. | Kalbiochem |
| Lipase TG | " | " |
| Protease (basic) | Bacillus subtilis | Kyowa Hakko |

These enzymes or microorganisms may be used in various forms, such as purified enzyme, crude enzyme, enzyme-containing products, microorganism culture broth, culture medium, cells, culture filtrate and products obtained by treating them, etc., depending on necessity. The enzyme and the microorganism may also be used in combination.

Upon practice of the method of the present invention, the mixture of Corey lactone diols of the formulae (Ia) and (Ib) as substrates is generally dissolved in an organic solvent and the acylating agent and the enzyme and/or the microorganism are added to the solution to react them, though the practice may vary depending upon the enzyme or microorganism used.

Any organic solvent may be used so long as it does not inactivate the enzyme or microorganism and does not react with the substrate and the ester produced. Examples of the organic solvent include methylene chloride, chloroform, 1,2-dichloroethane, hexane, benzene, diethyl ether, etc.

Examples of the acylating agent include fatty acid enol esters such as vinyl acetate, vinyl propionate, vinyl octanoate, 2-propylenyl acetate, etc., fatty acid esters such as tributyrin, butynic acid 1,1,1-trichloroethyl, etc.; fatty acid anhydrides such as acetic anhydride, etc.

The reaction is performed by stirring or shaking for an hour to several days. The reaction may be carried out at 5° C. to 50° C.; at a low temperature, the reaction is slow, but at a high temperature, the enzyme might be inactivated and the asymmetric selectivity might be lowered in some occasion. Therefore, the temperature is preferably between 10° C. and 35° C. After completion of the reaction, the remaining diol and the formed ester are separated from each other and purified in a conventional manner.

The mixture of the diols of the formulae (Ia) and (Ib):

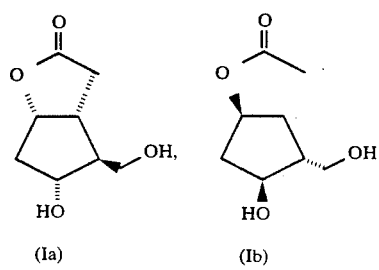

which are used as substrates can be prepared by known methods, etc. (for example, Tetrahedron Letters (TL), 4639 (1976)).

According to the method of the present invention, optically active Corey lactone diols which are used as intermediates for useful drugs, etc. can be subjected to optical resolution in one step. Therefore, the optically active Corey lactone diols and/or the formed acyl (e.g., acetyl) esters can be provided at low costs.

Hereinafter the present invention is described in more detail by referring to the examples but is not deemed to be limited thereto.

EXAMPLE 1

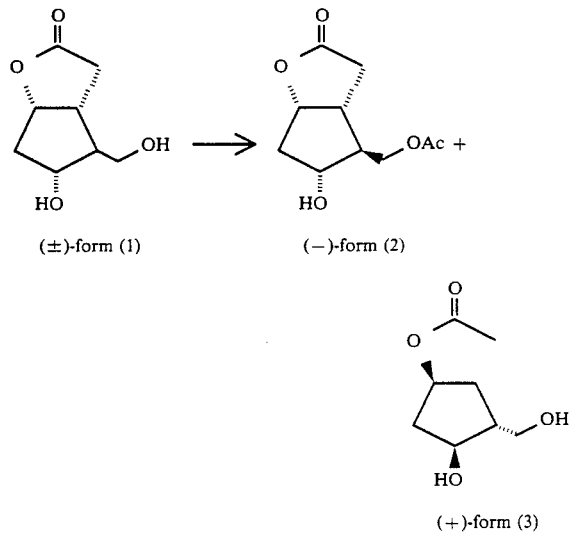

While stirring 508 mg (5.9 mmols) of vinyl acetate was added to a solution of 101.5 mg (6.59 mmols) of ($\pm$)-6$\beta$,7$\alpha$-dihydroxy-2-oxa-bicyclo[3.3.0]octan-3-one (1) in CH$_2$Cl$_2$ (10 ml) at room temperature and then 65 mg of lipase AK was added to the mixture. After stirring for 3 hours, the reaction mixture was filtered through Celite and the Celite layer was washed with 10% MeOH-CH$_2$Cl$_2$ solution (10 ml×5 times). The combined organic layer was distilled off under reduced pressure. The residue was subjected to silica gel (15 g) column chromatography. From the eluate with 50% hexane-ethyl acetate, 55.7 mg (44.1%) of oil (2) was obtained. Then 48 mg (47.3%) of oil (3) was obtained from the eluate with ethyl acetate and 2% MeOH-ethyl acetate.

Oil (2):
$[\alpha]_D$ −27.1° (c=0.842, MeOH);
IR (neat): 3460, 1760, 1731 cm$^{-1}$;
NMR (CDCl$_3$; 90 MHz): $\delta$ 2.08 (3H, s), 1.9–2.8 (7H, m), 4.0–4.2 (1H, m), 4.05 (1H, d, J=2.3 Hz) 4.12 (1H, d, J=2.3 Hz), 4.95 (1H, m).
Mass spectrometry (MS) (m/e): 215 (M$^+$+1), 171, 154, 136, 126, 95, 82, 54, 43 (100%).
High resolution mass spectrometry (MS): Calcd.: 215.0920 (as C$_{10}$H$_{15}$O$_5$ (M$^+$+1). Found: 215.0923.
Rf value: 0.45 (ethyl acetate); 0.60 (ethyl acetate:-MeOH=6:1).
Oil (3):
$[\alpha]_D$+29.9° (c=0.822, MeOH);
IR (neat): 3380, 1750 cm$^{-1}$;
NMR (CD$_3$OD; 90 MHz): $\delta$ 1.8–2.8 (6H, m), 3.5 (1H, d, J=2 Hz), 3.55 (1H, d, J=2 Hz), 4.10 (1H, q, J=5.7 Hz), 4.85 (2H, br, s), 5.00 (1H, m).
MS (m/e): 173 (M$^+$+1), 154, 126, 82, 54 (100%).
High resolution MS: Calcd.: 173.0814 (as C$_8$H$_{13}$O$_4$ (M$^+$+1)); Found: 173.0812.
Rf value: 0.05 (ethyl acetate); 0.45 (ethyl acetate:-MeOH=6:1).

The optical purity was determined according to the following scheme (with respect to MTPACl and MTPA in the reaction scheme, refer to Notes described below).

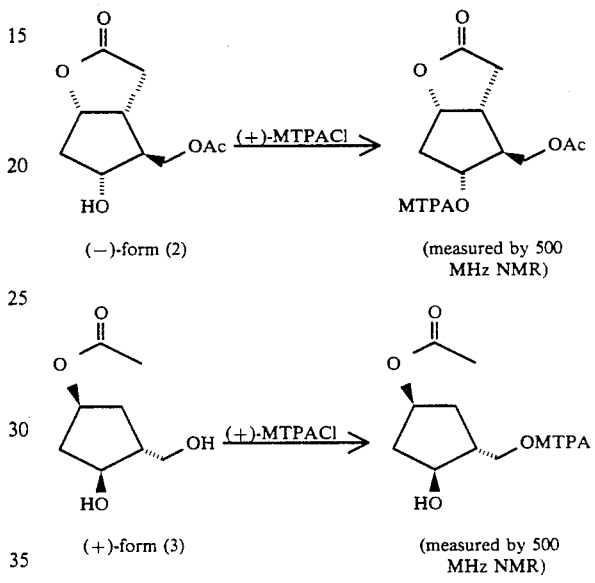

Notes:

MTPA = Phenyl-$\overset{\underset{|}{\text{CF}_3}}{\underset{|}{\text{C}}}$—CO—
$\qquad\qquad\quad$ OCH$_3$ MTPACl = Phenyl-$\overset{\underset{|}{\text{CF}_3}}{\underset{|}{\text{C}}}$—COCl
$\qquad\qquad\qquad$ OCH$_3$ Ac = CH$_3$CO
Me = CH$_3$

EXAMPLES 2 TO 5

Optical resolution was performed in a manner similar to Example 1 except for using 100 mg of ($\pm$)-(1), 0.50 g (10 equivalents) of vinyl acetate, 65 mg of lipase described in Table 2 and 10 ml of 1,2-dichloroethane. The results are shown in Table 2. In Example 4, 10 ml of tetrahydrofuran (THF) was used and 150 mg of Lipase Amano AK was used in Example 5.

TABLE 2

| Example No. | Starting Material (1) | Lipase (cf. Table 1) | Reaction Time (hour) | Product (2) | Product (3) |
|---|---|---|---|---|---|
| 2 | 100.8 mg | Lipase Amano PS | 3 | 58.5 mg (46.7%) $[\alpha]_D$ −17.7° (c = 0.94, MeOH) | 43.8 mg (43.4%) $[\alpha]_D$ +26.5° (c = 0.61, MeOH) |

TABLE 2-continued

| Example No. | Starting Material (1) | Lipase (cf. Table 1) | Reaction Time (hour) | Product (2) | Product (3) |
|---|---|---|---|---|---|
| 3 | 101.2 mg | PPL (Pig pancreatin lipase made by Shigma) | 46 | 29.7 mg (23.6%) $[\alpha]_D$ −21.5° (c = 0.594 MeOH) | 57.2 mg (56.5%) $[\alpha]_D$ +14.7° (c = 1.144, MeOH) |
| 4 | 100.3 mg | Lipase Amano AK | 2.5 | 47 mg (37.7%) $[\alpha]_D$ −18.86° (c = 0.94, MeOH) | 30.2 mg (30.1%) $[\alpha]_D$ +33.96° (c = 0.604, MeOH) |
| 5 | 100.8 mg | Lipase Amano AK | 1.45 | 52.6 mg (42%) $[\alpha]_D$ 25.31° (c = 1.052, MeOH) | 45.6 mg (45.2%) $[\alpha]_D$ +33.0° (c = 0.844, MeOH) |

What is claimed is:

1. A method for optical resolution of optically active Corey lactone diols comprising reacting a mixture of Corey lactone diols of formulae (Ia) and (Ib):

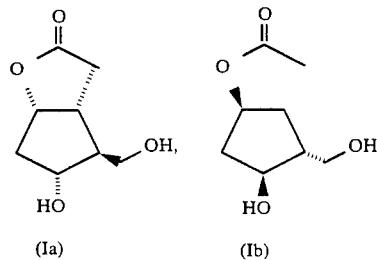

(Ia)   (Ib)

optically selectively with an acetylating agent in the presence of an enzyme capable of asymmetrically hydrolyzing an acetylester to acetylate only a primary hydroxy group of the diols, isolating a formed acetylester and purifying to selectively produce

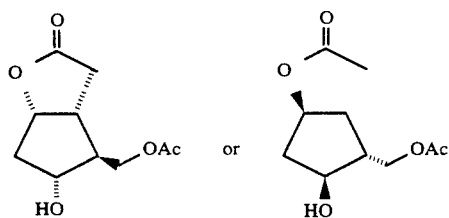

2. A method as claimed in claim 1, wherein said enzyme is an enzyme obtained from microorganism belonging to the genus Rhizopus, the genus Mucor, the genus Aspergillus, the genus Candida, the genus Pseudomonas, the genus Alcaligenes, the genus Acromobacter or the genus Bacillus or an animal organ.

3. A method as claimed in claim 1, comprising reacting a mixture of Corey lactone diols to selectively produce

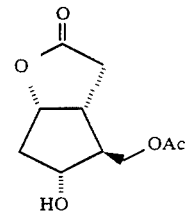

4. A method as claimed in claim 1, comprising reacting a mixture of Corey lactone diols to selectively produce

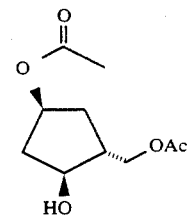

5. A method as claimed in claim 1, wherein said enzyme is obtained from a microorganism selected from the group consisting of lipase from Pseudomonas, lipase from Mucor sp., lipase from *Aspergillus niger*, liproprotein lipase from Pseudomonas sp., lipase from *Candida cyrindraceuous*, lipase from *Candida paralipolytica*, lipase from Acromobacter sp., lipase from Alcaligenes sp., olipase from *Rhizopus Japanicus*, lipase from *Rhizopus Japanicus*, lipase from *Rhizopus niveus*, lipase from *Rhizopus delemar*, protease from pig pancrease, pancreatin from pig pancrease, lipase from Rhizopus sp., and protease from *Bacillus subtilis*.

6. A method as claimed in claim 5, wherein the temperature is in the range of 5°-50° C.

7. A method as claimed in claim 6, wherein the temperature is in the range of 10°-35° C.

8. A method for optical resolution of optically active Corey lactone diols comprising reacting a mixture of Corey lactone diols of formulae (Ia) and (Ib):

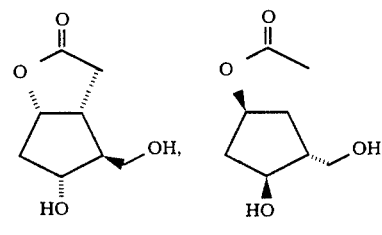

(Ia)   (Ib)

optically selectively with an acetylating agent in the presence of a microorganism belonging to a genus selected from the group consisting of Rhizopus, Mucor, Aspergillus, Candida, Pseudomonas, Alcaligenes, Acromobacter and Bacillus capable of symmetrically hydrolyzing an acetylester to acetylate only a primary hydroxy group of diols, to selectively produce

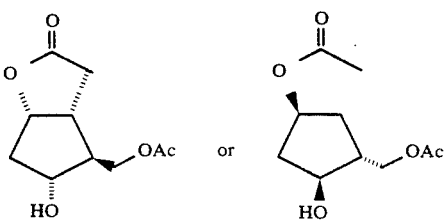

* * * * *